United States Patent [19]

Maizenberg et al.

[11] 4,309,905
[45] Jan. 12, 1982

[54] METHOD FOR DETECTING NON-UNIFORMITIES OF MAGNETIC MATERIALS AND DEVICE FOR EFFECTING SAME

[76] Inventors: Mikhail I. Maizenberg, ulitsa K. Marxa, 15/1, kv. 117; Mikhail D. Kaplan, ulitsa Iskry, 3, kv. 3; Stanislav V. Veremeenko, ulitsa Dimo, 17/1, kv. 35; Vladimir T. Bobrov, ulitsa Belskogo, 34/1, kv. 117; Vladimir U. Moshkovich, ulitsa Vossoedinenia, 5, kv. 67; Petr F. Shapovalov, bulvar K. Marxa, 10, kv. 13, all of, Kishinev; Vladimiru A. Troitsky, ulitsa Bratislavskaya, 8, kv. 86, Kiev; Petr G. Zhukovsky, ulitsa Belorusskaya, 15, kv. 67, Kiev; Igor B. Komsky, ulitsa Krasnoarmeiskaya, 67, kv. 20, Kiev, all of U.S.S.R.

[21] Appl. No.: 106,517

[22] Filed: Dec. 26, 1979

[51] Int. Cl.³ .............................................. G01N 29/04
[52] U.S. Cl. ....................................... 73/601; 73/643; 324/227
[58] Field of Search .................. 73/601, 643; 324/226, 324/227, 234, 235, 236, 237, 238, 239, 240

[56] References Cited

U.S. PATENT DOCUMENTS 4,215,310  7/1980  Schwerer ............................ 324/237

FOREIGN PATENT DOCUMENTS 2053185  4/1971  France ................................ 73/601

OTHER PUBLICATIONS

W. Lord et al., "Leakage Field Methods of Defect Detection", *International Journal of Nondestructive Testing*, vol. 4, pp. 249-274, 1972.
V. Klyuyev, "Instrumentation for Nondestructive Testing of Materials and Articles", *Machinostroyeniye Publishers*, pp. 11-13, 1976.
V. Kulyeev et al., "The Effect of Mechanical Strains on Some Properties of Magnetostriction Materials", 1972.

*Primary Examiner*—Stephen A. Kreitman
*Attorney, Agent, or Firm*—Fleit & Jacobson

[57] ABSTRACT

The method for detecting non-uniformities of magnetic materials resides in the use of the direct and inverse electromagnetic-acoustic conversion, effected in the zone of magnetic non-uniformities of magnetized articles. The method is characterized by effecting said conversion in an intermediate layer located in the vicinity of the material being inspected. As the intermediate layer, materials with great values of dynamic magnetostrictive constants are used. The use of the intermediate layer of a predetermined configuration enables estimation of the non-uniformity value not only singularly by the amplitude of the established elastic vibrations, but also by the number of recurrent pulses whose pulse-height distribution is conditioned by the damping factor of the intermediate layer. In the given device, as distinct from the conventional noise-suppressing devices, operating on the principle of decoding the coded signals, the parameters of the code are defined by the material and structure of the intermediate layer.

36 Claims, 12 Drawing Figures

METHOD FOR DETECTING NON-UNIFORMITIES OF MAGNETIC MATERIALS AND DEVICE FOR EFFECTING SAME

FIELD OF THE INVENTION

The present invention relates to ultrasonics and, more particularly, to methods and devices for detecting non-uniformities of magnetic materials.

The invention is applicable to nondestructive testing of magnetizable sheets, bands, pipes, rods and other items right on the production line where they can move at a speed of up to 10 meters per second. It is also applicable to systems for monitoring the relative location of an object under investigation in different production processes.

Finally, the invention is applicable to physico-mechanical and magnetic measurements.

BACKGROUND OF THE INVENTION

Today one of the basic problems of nondestructive testing of materials is the provision of methods and devices for detecting non-uniformities of magnetic materials, which would ensure a high rate, sensitivity and reliability of inspection.

The existing methods and devices for detecting non-uniformities of magnetic materials hinder the progress of technology and the rate of production, because they call for the use of costly equipment installed outside the production line. The need for advanced methods and devices is also due to increasingly stringent requirements as to the sensitivity to non-uniformities of materials when the testing is carried out at elevated temperatures of more than 100° C.

The existing methods and devices for nondestructive detection of non-uniformities of magnetic materials may be divided into two categories:

(1) methods and devices for ultrasonic testing;
(2) methods and devices for magnetic testing.

The methods which fall under the first category (cf. "Pribory dlya nerazrushayushchego controlya materialov i izdeliy" ("Instrumentation of Nondestructive Testing of Materials and Articles"), ed. by V. V. Klyuyev, Machinostroyeniye Publishers, Moscow, 1976, pp. 201–234) are based on the excitation of ultrasonic vibration in the material under investigation. The ulrasonic vibration interacts with non-uniformities in the material, and the resultant signals are recorded.

This method is carried out with the aid of devices of the type that comprises a material to be investigated, piezoelectric converters and means to provide an acoustic contact with the surface of the material.

The ultrasonic vibration is produced and received by the piezoelectric converters which are of the contact or immersion type.

The foregoing method can be also carried out with the aid of a device where electromagnetic-acoustic converters are used instead of the piezoelectric converters. Such a device includes a magnetizing system and a conductor through which current is passed and which extends in a magnetic field in parallel with the surface of the material under inspection. Ultrasound is produced by the action on the surface of the material being tested of electromagnetic oscillation coming from the conductor.

The methods and devices of the first category necessitate an acoustic contact between the piezoelectric converters and the article being tested; it is also necessary that the piezoelectric elements should be pasted to prisms. These factors put limitation on the temperature of the article under investigation and on the rate of testing. The application of electromagnetic-acoustic converters is limited by their low sensitivity which depends, among other things, on specific characteristics of artcles being tested, such as the dynamic magnetostriction constants.

The magnetic testing methods which fall under the second category (cf. "Pribory dlya nerazrushayushchego controlya materialov i izdeliy" ("Instrumentation for Nondestructive Testing of Materials and Articles"), ed. by V. V. Klyuyev, Machinostroyeniye Publishers, Moscow, 1976, pp. 30–71) are based on detecting and recording local distortions of the magnetic field produced by the magnetizing system in the presence of non-uniformities in the material being tested. Such methods are effected with the aid of devices of the type that comprises a material to be tested, a magnetizing system (inductance coils, ferroprobes, Hall elements, etc.), magnetosensitive elements and an indication system.

The methods and devices of the second category show a low sensitivity in detecting internal non-uniformities. This is due to a low signal-to-noise ratio which, in turn, is due to the impossibility of separating the useful signal from the magnetostructural noise. In addition, such methods involve the difficulty of converting constant magnetic fields of non-uniformities to high-frequency signals with the use of inductance coils, ferroprobes, etc.

There is known a defect detection method and device (cf. W. Lord and D. J. Oswald, Leakage Field Methods of Defect Detection, in International Journal of Nondestructive Testing. 1972, Vol. 4, pp. 249–274).

According to this method, a material to be tested is placed in a steady magnetic field which is partially distorted by a local non-uniformity in the material to extend as far as above the surface of the article being tested, i.e., to produce a leakage field.

The above method is carried out with the aid of a device comprising a magnetic material, a magnetizing system which is a permanent magnet or an electromagnet, as well as a magnetosensitive element which converts the local non-uniformity field to an electric signal, an amplifier and a recording system.

A non-uniformity or defect in the material being tested causes a redistribution of the magnetic field, which is detected by the magnetosensitive element.

The above method and device are disadvantageous in their low sensitivity in the case of internal non-uniformities, as well as low reliability of testing due to a low signal-to-noise ratio.

There is further known a method for detecting non-uniformities of magnetic materials (cf. French Pat. No. 2,053,185, Cl. G 01/n and G 0.1/n 29/00, filed on July 24, 1970), comprising placing a material to be tested in a magnetic field and acting by vibration on the surface of a magnetostrictive medium arranged in proximity to the non-uniformity zone of the material, which is followed by recording signals resulting from the electromagnetic-acoustic conversion taking place in the medium. Ultrasonic vibration is used to act on the surface of the material under investigation which is the magnetostriction medium.

Ultrasonic vibrations propagate in the magnetic material to interact with a non-uniformity. This results in an electromagnetic-acoustic conversion due to the magnetostriction, which means that the steady magnetic fields of the non-uniformities are modulated by the ultrasonic vibrations at an ultrasonic frequency to become variable magnetic fields which are recorded.

The latter method is carried out with the aid of a device which comprises a magnetizing system whereof the magnetic flux is passed through a magnetostrictive medium found in proximity to the non-uniformity zone of the material under investigation. The device further contains two converters mounted on the surface of the magnetostrictive medium and electrically coupled to a main radio-wave pulse generator and to a main amplifier connected to an indicator. One of the converters is piezoelectric and connected to the main radio-wave pulse generator. The second converter is an inductance coil which is connected to the main amplifier.

The main radio-wave pulse generator excites the piezoelectric converter which generates ultrasonic vibrations in the material being tested. The ultrasonic vibrations change the steady magnetic fields into variable fields which are detected by the inductance coil and then amplified and recorded.

The latter method and device are disadvantageous in that they are incapable of detecting internal non-uniformities. This is due to the fact that the variable magnetic fields caused by internal non-uniformities are screened because of the skin effect. Besides, this method does not make it possible to test materials with relatively high dynamic magnetostriction levels, which accounts for a limited range of materials that can be tested. If the device for effecting this method makes use of piezoelectric converters, provision has to be made for an acoustic contact of these converters with the material being tested. However, such a requirement imposes limitations on the rate of testing and on the temperature of the material.

SUMMARY OF THE INVENTION

It is an object of the present invention to provide a method for detecting non-uniformities of magnetic materials, which would make it possible to detect both external and internal non-uniformities in materials being tested.

It is another object of the invention to improve the sensitivity and reliability of non-uniformity detection.

It is still another object of the invention to expand the range of materials to be tested.

It is yet another object of the invention to raise the rate of testing and make it possible to test materials at elevated temperatures.

It is a further object of the invention to provide a simple and reliable device for detecting non-uniformities in magnetic materials.

Finally, it is an object of the present invention to improve the noise immunity of such a device.

To the accomplishment of the foregoing and related ends, the invention consists in providing a method for detecting non-uniformities in magnetic materials, which comprises placing a material to be tested in a magnetic field and using vibration or oscillation to act on the surface of a magnetostrictive medium arranged close to the non-uniformity zone of the material, which is followed by recording signals resulting from the electromagnetic-acoustic conversion, which method is characterized, according to the invention, in that the vibration is acoustic vibration whereof the polarization vector contains a component which is normal to the surface of the magnetostrictive medium, or in that use is made of electromagnetic oscillation whereof the polarization vector is perpendicular to the magnetic field vector, or in that use is made of a combination of ultrasonic vibration and electromagnetic oscillation polarized in the above manner.

It is advisable that the electromagnetic-acoustic conversion of ultrasonic vibration or electromagnetic oscillation, or of a combination of both should be effected in a magnetic field whereof the intensity corresponds to a maximum dynamic magnetostriction constant in the material under investigation.

It is preferable that the function of the magnetostrictive medium should be performed by an intermediate layer arranged in proximity to the material being tested, which intermediate layer is acted upon by ultrasonic vibration or electromagnetic oscillation, or a combination of both.

It is desirable that the intermediate layer should be a material whereof the dynamic magnetostriction constant is not lower than that of the permendur.

It is advisable that at a predetermined frequency of ultrasonic vibration or electromagnetic oscillation, or a combination of both, the thickness of the intermediate layer should be selected with reference to the dispersion curves of normal ultrasonic waves in that layer.

It is expedient that the intermediate layer should be additionally magnetized at least in the recording zone so that the lines of the additional magnetic field are perpendicular to the surface of that layer.

It is advisable that in the case of using ultrasonic vibration to act on the intermediate layer, a second layer similar to the first one should be arranged in proximity to said first layer on the side opposite to the one of which the first intermediate layer is acted upon by ultrasonic vibration, and that one should then record ultrasonic vibration caused in the second intermediate layer by electromagnetic oscillation produced in the intermediate layer opposite the non-uniformity zone in the material being tested.

It is advisable that ultrasonic vibration in the second intermediate layer should be additionally recorded in the zone on the side opposite to the recording zone in the same intermediate layer.

The objects of the present invention are further attained by providing a device for detecting non-uniformities in magnetic materials, which is intended to carry out the foregoing method and comprises a magnetizing system whereof the magnetic flux is passed through a magnetostrictive medium arranged in proximity to the non-uniformity zone of the material being tested, and two converters mounted on the surface of the magnetostrictive medium and electrically connected to a main radio-wave pulse generator and to a main amplifier coupled to an indicator, which device is characterized, according to the invention, in that it includes an auxiliary radio-wave pulse generator, an auxiliary amplifier and a switching unit which are all electrically interconnected so that if the magnetostrictive medium is acted upon by ultrasonic vibration or electromagnetic oscillation, one of the converters is connected via the switching unit to the main radio-wave pulse generator, while the second converter is connected via the same switching unit to the main amplifier, and if the magnetostrictive medium is simultaneously acted upon by ultrasonic vibration and electromagnetic oscillation, one of the converters is connected via the switching unit to the main radio-wave pulse generator and to the auxiliary amplifier, whereas the second converter is connected via the same switching unit to the auxiliary radio-wave pulse generator and to the main amplifier.

It is desirable that the magnetostrictive medium should be a strip arranged in proximity to the surface of the material being tested.

It is expedient that in the case the strip is simultaneously acted upon by ultrasonic vibration and electromagnetic oscillation, it should be shaped as a disc and that one of the converters should be arranged in the center of the disc.

It is preferable that the device should include a pulse counter and a comparator connected in parallel with the main amplifier.

It is advisable that in case the material being tested has at least one bend, the surface of the strip should be congruent to the surface of the material being tested, and that one of the converters should be constructed as at least one solenoid encompassing the strip at the bend.

It is advisable that the device should contain a controlled electromagnet placed in proximity to one of the converters so that the lines of the magnetic field produced by this electromagnet are perpendicular to the surface of the strip in the vicinity of said converter.

It is desirable that in the case the magnetostrictive medium is acted upon by ultrasonic vibration, a second strip, coplanar with the first strip, should be arranged in proximity to said first strip, and that the second converter should be mounted on said second strip on the side opposite to that of the converter mounted on the strip which is closer to the material being tested.

It is expedient that the device should include an intervalometer connected to the auxiliary amplifier, and another converter mounted on the second strip on the side opposite to that on which the converter is mounted on the same strip, which additional converter is connected via the switching unit to the auxiliary amplifier.

The method and device according to the invention for detecting non-uniformities in magnetic materials provide for a highly accurate and reliable detection of non-uniformities distributed over the entire thickness of the material under investigation. The method and device according to the invention make it possible to test magnetic materials with different magnetostriction constants at elevated temperatures of more than 100° C. and at a high rate of up to 10 meters per second without scanning the material being tested. The method and device of this invention are applicable to production lines which turn out sheet materials, pipes, bars, wire, etc. The device according to the invention is both simple and reliable and can operate in conjunction with any existing ultrasonic flaw detectors at high noise levels typical of today's industrial enterprises.

BRIEF DESCRIPTION OF THE ACCOMPANYING DRAWINGS

Other objects and advantages of the present invention will become more apparent from a consideration of the following detailed description of preferred embodiments thereof, taken in conjunction with the accompanying drawings, wherein.

DETAILED DESCRIPTION OF THE INVENTION

According to the invention, the method for detecting non-uniformities in magnetic materials consists in placing a material to be tested in a magnetic field and acting on the surface of a magnetostrictive medium arranged in proximity to the non-uniformity zone of the material by ultrasonic vibration whereof the polarization vector contains a component normal to the surface of the magnetostrictive medium, or by electromagnetic oscillation whereof the polarization vector is perpendicular to the magnetic field vector, or by a combination of ultrasonic vibration and electromagnetic oscillation polarized in the above manner, which is followed by recording signals resulting from the electromagnetic-acoustic conversion in the medium.

Figure 1:
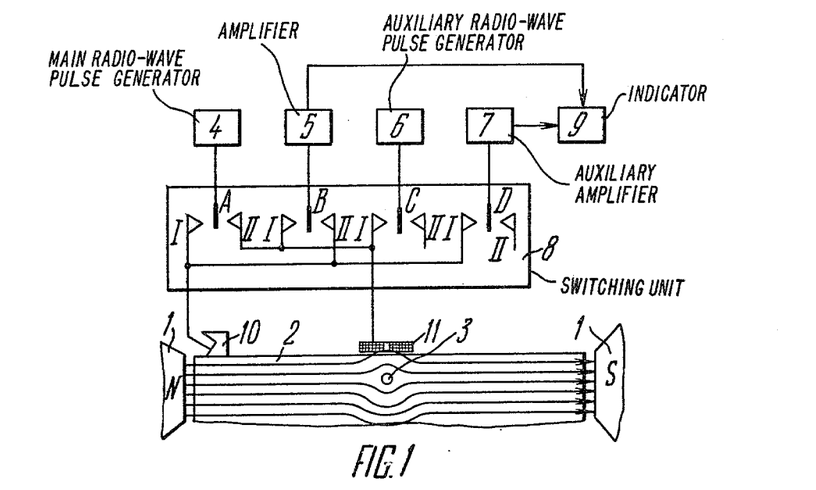
FIG. 1 is a block diagram of a device for detecting non-uniformities in magnetic materials, in accordance with the invention, which is intended to carry out the method according to the invention and wherein the magnetostrictive medium is the material being investigated.

The method according to the invention is carried out with the aid of a device comprising a magnetizing system 1 (FIG. 1) whereof the magnetic flux is passed through a magnetostrictive medium 2 arranged in proximity to a non-uniformity zone 3 of a material to be tested. In the embodiment under review, the function of the magnetostrictive medium 2 is performed by the material being tested which is further designated as 2. The device further includes a main radio-wave pulse generator 4, an amplifier 5, an auxiliary radio-wave pulse generator 6 and an auxiliary amplifier 7 which are connected to a switching unit 8. The amplifiers 5 and 7 are connected to an indicator 9. Converters 10 and 11 are mounted on the surface of the magnetic material 2 and connected to the switching unit 8. In the embodiment under review, the switching unit 8 comprises a set of three-point switches A, B, C and D which are respectively connected to the main generator 4, auxiliary generator 6 and amplifiers 5 and 7 having working positions I and II. The switching unit 8 may also be composed of polarized relays and other switching elements. In the embodiment under review, the converter 10 is a piezoelectric converter, and the converter 11 is a flat inductance coil. According to alternative embodiments, the converters 10 and 11 are of the electromagnetic-acoustic type.

Figure 2:
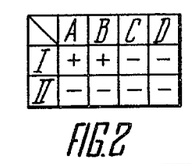
FIG. 2 shows the position of contacts of the switching unit of FIG. 1 for the case when the magnetostrictive medium is acted upon by ultrasonic vibration, in accordance with the invention.

If the magnetostrictive medium is acted upon by ultrasonic vibration, the switches A, B, C and D of the switching unit 8 (FIG. 1) assume the positions shown in FIG. 2.

In FIG. 2 and other attached drawings, "+" means a made contact, and "−" means a broken contact.

The converter 10 is connected via the switching unit 8 to the main generator 4. The converter 11 is connected to the main amplifier 5.

As the material 2 to be tested is magnetized, a leakage field is produced due to the non-uniformities 3. The converter 10 and main generator 4 produce ultrasonic vibration in the magnetic material 2. The polarization vector of this ultrasonic vibrations contains a component which is normal to the surface of the magnetic material 2.

As the converters 10 and 11 scan the surface of the material 2, the magnetostriction effect is produced and the ultrasonic vibrations modulate the steady magnetic fields of the non-uniformities 3 to convert them to electromagnetic oscillations which are received by the converter 11, amplified by the main amplifier 5 and transmitted to the indicator 9.

The polarization of ultrasonic vibrations is selected as follows. If the material 2 contains an internal non-uniformity 3, the leakage field is caused by effective "magnetic charges" produced in the zone of the non-uniformity 3. As pointed out above, the ultrasonic vibrations modulate, due to the magnetostriction, the density of the "magnetic charges" and, consequently, the field produced by these charges. If, however, the non-uniformity 3 is far from the surface of the material 2, for example, if it is spaced from the surface by a distance greater than the thickness of the skin layer where electromagnetic oscillation is attenuated, no useful signal is detected by the converter 11. Nevertheless it is possible to detect internal non-uniformities 3 which lie deeper than the skin layer, because the magnetic field, caused by the "magnetic charges" of the non-uniformity 3 inside the material 2, forms secondary "magnetic charges" on the surface of said material 2. Ultrasonic modulation of these secondary "charges" accounts for electromagnetic oscillation which is detected by the converter 11. Because of the longitudinal magnetostriction in the material 2, the secondary surface "charges" can only be modulated by acoustic vibration whereof the polarization vector contains a component normal to the surface of the magnetic material 2. No modulation is produced, for example, by longitudinal waves which travel parallel to the surface of the material 2 and whereof the normal polarization vector component is zero. On the contrary, surface Rayleigh waves, which contain a polarization component normal to the surface, do detect the non-uniformity 3; this equally applies to normal waves in confined media, which generally contain a required polarization component. Thus the proposed selection of polarization of ultrasonic vibrations makes it possible to detect internal non-uniformities 3.

Figure 3:
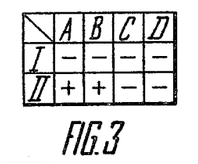
FIG. 3 shows the position of contacts of the switching unit of FIG. 1 for the case when the magnetostrictive medium is acted upon by electromagnetic oscillation, in accordance with the invention.

If the magnetostrictive medium is acted upon by electromagnetic oscillation, the contacts of the switches A, B, C and D of the switching means 8 (FIG. 1) assume the positions shown in FIG. 3.

In this case the converter 11 is connected to the main generator 4, and the converter 10 is connected to the main amplifier 5.

As the converters 10 and 11 scan the surface of the material 2 being investigated, the converter 11 and main generator 4 produce electromagnetic oscillations. Due to the magnetostriction effect and the magnetic field of the non-uniformity 3, the electromagnetic oscillations produce ultrasonic vibrations in the material 2, which are detected by the converter 10, amplified by the main amplifier 5 and transmitted to the indicator 9. The polarization of the electromagnetic field is selected so that the vector of the steady magnetizing field is perpendicular to the vector of the variable magnetic field in the electromagnetic wave. As a result, no ultrasound is produced in the material 2 unless there is a non-uniformity 3 in that material. However, the distribution of the magnetic field in the material 2 changes in the presence of a non-uniformity 3, and new magnetic field components are brought about, making it possible to produce ultrasound. If the electromagnetic wave polarization is different from the one described above and if ultrasound is produced even in the absence of a non-uniformity 3, the appearance of a non-uniformity 3 causes a change in the amplitude of ultrasound. This change is also an indication of a non-uniformity 3, although in such a case the signal-to-noise ratio is far worse than it should be. The method according to the invention makes it possible to detect both external and internal non-uniformities 3. It must be pointed out that the amplitude of ultrasound, which is indicative of the presence of a non-uniformity 3, is higher than the amplitude of the useful acoustic signal normally observed while carrying out conventional testing methods, because unlike these conventional methods, the recorded acoustic wave is not the result of scattering of ultrasound by the non-uniformity 3. It must further be pointed out that the method according to the present invention is such that the directional diagram of ultrasound caused by the non-uniformity 3 may be formed by the converter 11, because the converter 10, which records the acoustic vibration, is within the maximum radiation zone. As far as the known testing methods and devices are concerned, the directional diagram of scattered ultrasound is formed by the non-uniformity 3 whereof the orientation and size are not known in advance; as a result, only a small portion of scattered acoustic energy is detected and recorded.

Figure 4:
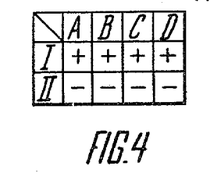
FIG. 4 shows the position of contacts of the switching unit of FIG. 1 for the case when the magnetostrictive medium is simultaneously acted upon by ultrasonic vibration and electromagnetic oscillation, in accordance with the invention.

If the magnetostrictive medium is simultaneously acted upon by ultrasonic vibration and electromagnetic oscillation, the switches A, B, C and D of the switching unit 8 (FIG. 1) assume the positions as shown in FIG. 4.

In this case the converter 10 is connected to the main generator 4 and auxiliary amplifier 7, while the converter 11 is connected to the main amplifier 5 and auxiliary generator 6.

As the converters 10 and 11 scan the surface of the material 2 being tested, the converter 10 and main generator 4 produce ultrasonic vibrations of the aforesaid polarization in the material 2. In the presence of a non-uniformity 3, the ultrasonic vibrations convert the static magnetic fields of the non-uniformity 3 to electromagnetic oscillations which are detected and recorded by the converter 11. The electromagnetic oscillations are amplified by the main amplifier 5 and transmitted to the indicator 9. The above process is accompanied by the following sequence of events: the converter 11 and auxiliary generator 6 act on the magnetic material 2 with electromagnetic oscillations of the above-mentioned polarity; a non-uniformity 3 produces acoustic vibrations in the material 2, which are detected by the converter 10 and successively transmitted to the auxiliary amplifier 7 and indicator 9.

The action on the magnetostrictive medium by a combination of ultrasonic vibration and electromagnetic oscillation produces two useful signals all at the same time, which improves the noise immunity and accuracy of measurements.

As pointed out above, the method according to the invention for detecting non-uniformities of magnetic materials necessitates magnetostriction which, in turn, causes electromagnetic-acoustic transformation of oscillations on the surface of the material being tested, which are polarized in a certain manner. It can be inferred from the above statement that a direct interaction between oscillations and a non-uniformity is not at all indispensable. Unlike conventional ultrasonic testing techniques, the method according to the invention makes it unnecessary to satisfy this condition: $f \leq L$, where f is the oscillation frequency and L is the typical grain size of the material.

On the other hand, the testing of coarse-grained materials is seriously hampered due to the scattering of ultrasound by individual grains, which scattering increases with an increase of the frequency f. The oscillation frequency f may be selected so as to satisfy this condition:

$$f = C_f/L,$$

where
 f is the oscillation frequency; and
 $C_f$ is the phase velocity of propagation of ultrasound in the material under investigation.

The selection of the frequency in the above manner accounts for a significant reduction of structural noise and enables one to inspect coarse-grained materials.

Figure 5:
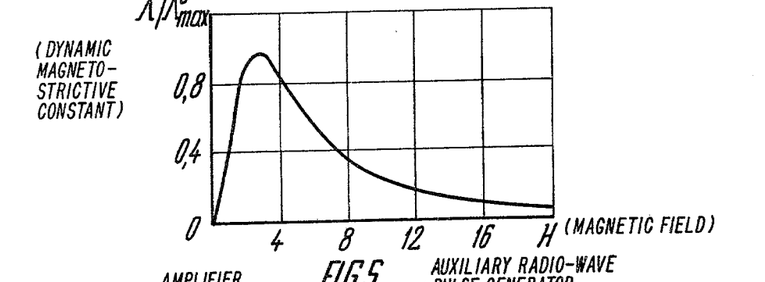
FIG. 5 is a graph showing a typical relation between the relative dynamic magnetostriction constant and the magnetic field intensity.

The ultrasonic modulation of the steady magnetic fields of non-uniformities and the production of ultrasound by electromagnetic oscillations in the presence of non-uniformities are due to the magnetostrictive nature of the medium. If the magnetostrictive medium is acted upon by ultrasonic vibration, the resultant conversion takes place due to the reverse magnetostriction effect; if the magnetostrictive medium is acted upon by electromagnetic oscillation, ultrasound is produced due to the direct magnetostriction effect. It is generally known (cf. "Physica metallov i metallovedeniye" ("Physics of Metals and Physical Metallurgy"), 1972, Vol. 33, Series 2, p. 227) that in most magnetic metals, such as magnet steel, the direct and reverse dynamic magnetostriction constants are extremely dependent on the intensity of the steady magnetic field. FIG. 5 shows a typical relationship between the relative direct dynamic magnetostriction constant $\lambda/\lambda°_{max}$, plotted as the ordinates, and the magnetic field intensity H measured in oersteds and plotted as the abscissas, where $\lambda°_{max}$ is a maximum value of the direct dynamic magnetostriction constant. It follows that the magnetic field intensity should be selected so as to maximize the dynamic magnetostriction constant and thus optimize the electromagnetic-acoustic transformation. The conventional magnetic flaw detection methods use maximum possible magnetic field intensities, which may be so high as to saturate the magnetic material. According to the method of the present invention, the optimum magnetic field intensity H is in the range of a few oersteds to a few tens or scores of oersteds; these values are much lower than those stipulated by the conventional methods and which are as high as $10^3$ to $10^5$ oersteds. It follows that the method according to the present invention is such that one can select the magnetic field intensity so as to maximize the dynamic magnetostriction constant and thus maximize the effectiveness of the transformation; this also means more lenient requirements imposed on the magnetizing system in view of a reduced magnetic field intensity.

Figure 6:
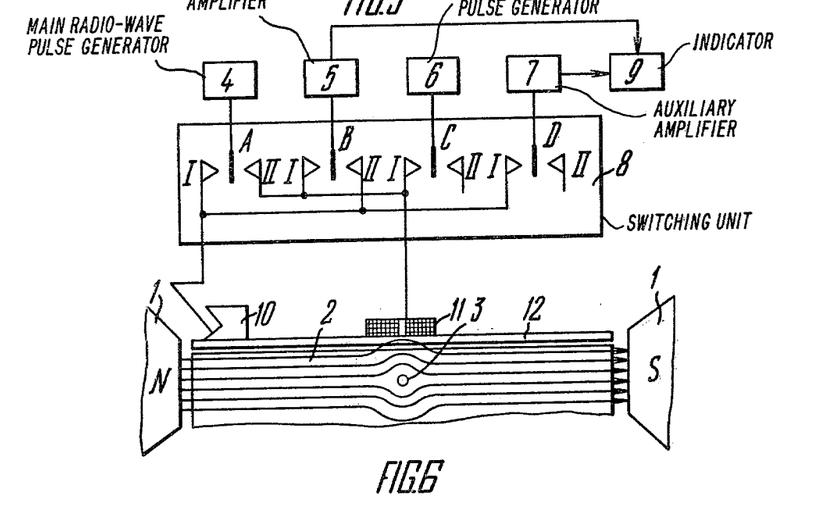
FIG. 6 is a diagram of a device for carrying out the method according to the invention, wherein the magnetostrictive medium is a strip.

FIG. 6 is a schematic view of a device for detecting non-uniformities of magnetic materials, in accordance with the invention, where the function of the magnetostrictive medium is performed by an intermediate layer 12. This layer 12 is a strip which will be further designated as 12.

If the function of the magnetostrictive medium is performed by an intermediate layer acted upon by ultrasonic vibrations or electromagnetic oscillations, or a combination of both, the switches A, B, C and D of the switching means 8 are in positions shown in FIGS. 2, 3 and 4.

Consider, by way of an example, operation of the device for the commonest case when the strip 12 is simultaneously acted upon by ultrasonic vibrations and electromagnetic oscillations; the positions of the switches A, B, C and D are shown in FIG. 4.

The main generator 4 and converter 10 produce ultrasonic vibrations in the strip 12, which propagate in said strip 12 to be converted above the non-uniformity zone 3 of the material 2 being tested to electromagnetic oscillations which are received by the main amplifier 5 and transmitted therefrom to the indicator 9. As this takes place, the auxiliary generator 6 and converter 11 produce electromagnetic oscillations; in the presence of a non-uniformity 3, these are converted in the strip 12 to ultrasonic vibrations which are detected by the converter 10 and amplified by the auxiliary amplifier 7.

As pointed out above, the method according to the invention dispenses with a direct interaction between the oscillations and non-uniformities 3. As a result, the function of the magnetostrictive medium can be performed by the strip 12 arranged in proximity to the material 2 being tested. The effective "magnetic charges" on the surface of the material 2 produce a magnetic field which, in its turn, forms "magnetic charges" on the surface of the strip 12. As the strip 12 is acted upon by ultrasonic vibrations or electromagnetic oscillations, or a combination of both, the magnetic non-uniformity area of the strip 12, which non-uniformity is the result of secondary "magnetic charges", is the site of a transformation of the waves to electromagnetic or acoustic, respectively, which are then detected and recorded. The use of the strip 12 as the magnetostrictive medium accounts for a contactless inspection method which remains such even if the converter 10 is of the piezoelectric type. If that be the case, the converter 10 and the inductance-type converter 11 are mounted on the surface of the strip 12 to combine into a single unit for detecting non-uniformities 3 in the material 2 under investigation.

The effectiveness of the proposed method is largely determined by the value of the dynamic magnetostriction constant of the material being tested. The use of an intermediate layer where the electromagnetic-acoustic transformation due to magnetostriction takes place, accounts for a high effectiveness of such a transformation if the dynamic magnetostriction constant $\lambda$ of the material of this intermediate layer is not lower than the corresponding value $\lambda_p$ of the permendur. Thus the method of this invention is effective even in testing magnetic materials possessing extremely low dynamic magnetostriction constants ($\lambda \leq \lambda_p$).

Figures 7, 8:
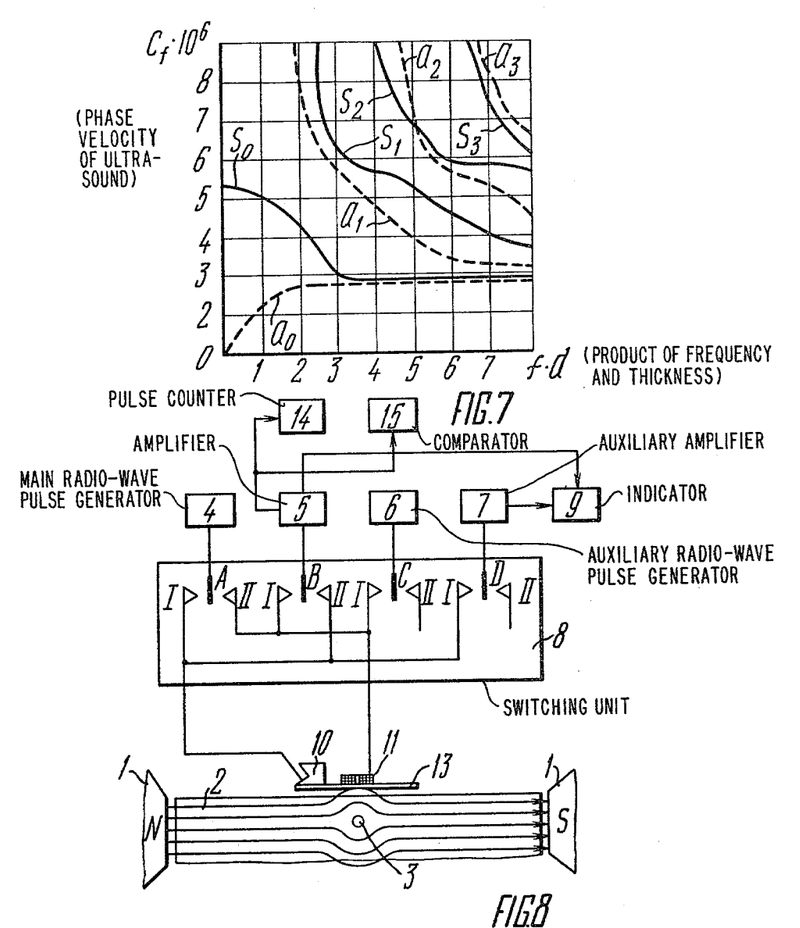
FIG. 7 is a graph showing typical dispersion curves for normal ultrasonic waves in the layer.
FIG. 8 is a diagram of the device of FIG. 6 with a disc-shaped strip, in accordance with the invention.

In detecting non-uniformities of magnetic materials according to the proposed method, the oscillations should be polarized as described above. It must be remembered in this connection that the intermediate layer may be the site of propagation of different types of oscillations, including symmetric and antisymmetric Lamb waves, transverse SH waves and surface waves. The type of the wave propagating in the layer and the distribution in that wave of particle displacement components are determined by the product of the oscillation frequency times the layer thickness. This is expressed mathematically by dispersion curves for the waves in the layer. These curves express the relationship between the ultrasound phase velocities $C_f$ and the product of the frequency f by the layer thickness. FIG. 7 shows typical curves for Lamb waves in a layer with a Poisson ratio $\nu = 0.29$. Plotted as the abscissas is the product of fd MHz.mm; $C_f 10^6$ mm/sec is plotted on the y-axis. The curves $a_0$, $a_1$, $a_2$ and $a_3$, shown by the dash lines, correspond to zero, first, second and third antisymmetric modes, respectively; the curves $s_0$, $s_1$, $s_2$ and $s_3$ correspond to zero, first, second and third symmetric modes shown by the solid line.

The following example will serve to illustrate the selection of the thickness of the strip 12 (FIG. 6). The non-uniformity 3 is detected at an ultrasonic oscillation frequency f=2.5 MHz and with reference to the curve $s_0$ corresponding to zero symmetric modes. The $s_0$ wave contains required polarization vector components in the range fd (oersteds) of 0.8 to 1.5 MHz/mm. With f=2.5 MHz, the thickness of the strip 12 is 0.3 to 0.6 mm.

The foregoing way of selecting the thickness of the intermediate layer provides for oscillations of the desired polarity and thus improves the effectiveness of the method.

FIG. 8 is a schematic view of a device in accordance with the invention, which is used in the case when a strip 13 is simultaneously acted upon by ultrasonic vibration and electromagnetic oscillation. The strip 13 is shaped as a disc; the converter 11 is placed in the center of the disc and constructed as a round inductance coil whereof the turns are concentric with the disc circumference.

The device of FIG. 8 further includes a pulse counter 14 intended to count the pulses received by the main amplifier 5, as well as a comparator 15 placed in parallel with the main amplifier 5.

Figure 9:
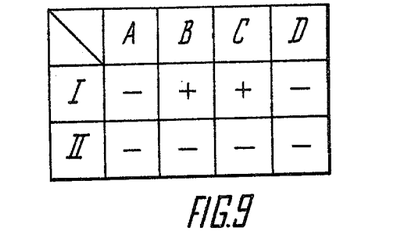
FIG. 9 shows the position of contacts as in FIG. 4 for the case when the strip is disc-shaped, in accordance with the invention.

The positions of the switches A, B, C and D of the switching unit 8 of the device of FIG. 8 are shown in FIG. 9.

The auxiliary generator 6 and converter 11 of this device generate electromagnetic oscillations to act upon the center of the disc 13 and produce ultrasonic vibrations, provided there are non-uniformities 3; the ultrasonic vibrations are reflected from the edges of the disc to converge in its center and be converted to electromagnetic oscillations which are detected by the converter 11, amplified by the main amplifier 5 and applied therefrom to the indicator 9 and to the pulse counter 14 and comparator 15.

The disc 13 (FIG. 8) makes it possible to record the whole energy of the acoustic vibrations produced in the zone of the non-uniformity 3 irrespective of the direction of ultrasound propagation. In the presence of a non-uniformity 3, the converter 11 records ultrasonic vibrations which are repeatedly reflected from the edges of the disc.

The repeated reflection of the signal is due to the fact that the acoustic vibrations produced in the disc are reflected may times from the edges of the disc and repeatedly pass through the center of the disc, each time producing a signal indicative of the presence of a non-uniformity 3. The greater the energy of ultrasound, the greater the number of such signals; in other words, the greater the size of the non-uniformity 3, the greater the number of such signals. The pulse counter 14 counts the number of such signals and thus furnishes information on the size of the non-uniformity 3.

As these multiple signals arrive at the comparator 15, the latter evaluates the relative magnitude of pulses which are next to each other. This magnitude is determined by the attenuation of acoustic waves in the material of the disc 13, which is either known or may be calculated in advance. The relative reduction of ultrasound amplitudes is entered in the comparator 15 to be compared with the relative value, which makes it possible to separate the useful signal from the noise.

Thus the circuitry of the device of FIG. 8 helps to improve the noise immunity of the device and makes it possible to determine the sizes of non-uniformities 3.

Figure 10:
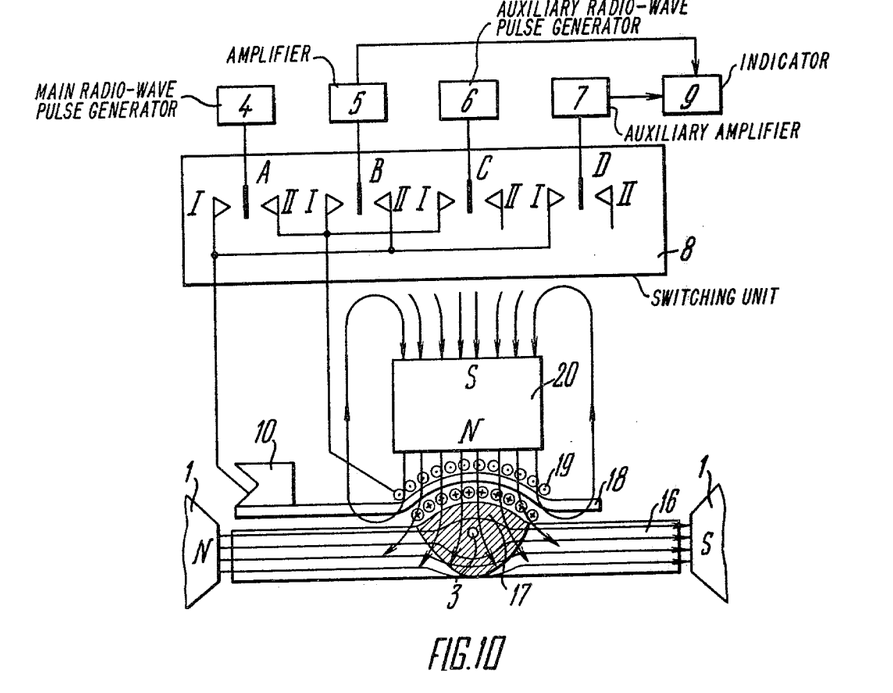
FIG. 10 is a diagram of a device as in FIG. 6 for the case of testing a material with a curvilinear surface and magnetizing the strip by an electromagnet, in accordance with the invention.

FIG. 10 is a schematic view of an alternative embodiment of the device in accordance with the invention, which is used in cases when a material 16 to be tested has a bend 17 and when the surface of a strip 18 is congruent with that of the material 16. A converter 19 is a solenoid encompassing the strip 18 at the bend 17.

The device of FIG. 10 further includes a controlled electromagnet 20 arranged in proximity to the converter 19 so that the lines of its magnetic field are perpendicular to the surface of the strip 18 where the converter 19 is located. In the case under review, the shape of the strip 18 is congruent with that of a reinforcing bead in the material 16.

The positions of the switches A, B, C and D of the switching unit 8 of the device of FIG. 10 are shown in FIGS. 2, 3 and 4.

If the device according to the invention uses the flat strip 12 (FIG. 6) to detect non-uniformities 3 in the magnetic material 16 having a bent surface, a non-uniform gap is produced between said strip 12 and material 16, whereby the sensitivity of the device to the non-uniformities 3 varies according to their coordinates. However, if use is made of the strip 18 whose surface is congruent with that of the material 16 and if the converter 19 is a solenoid which envelops the strip 18 at its bend 17, the gap between the strip 18 and material 16 is uniform, which accounts for an equal sensitivity of the device to the non-uniformities 3 in the material 16.

The device according to FIG. 10 is especially advantageous for detecting non-uniformities 3 in magnetic welds where the bend 17 of the material 16 is actually a reinforcing bead.

In the case of testing cylinder-shaped articles, such as pipes, rods, wire, etc., the strip 18 is shaped into a cylinder whereof the surface is congruent with that of the material 16 being tested.

The latter version of the device includes an auxiliary electromagnet 20 which interacts with the static magnetic fields of the non-uniformities 3 and amplifies them. By varying current passed through the winding of the electromagnet 20, one can vary the intensity of the field.

The use of the controlled electromagnet 20 whereof the field lines are perpendicular to the surface of the strip 18 makes it possible to increase the amplitude of recorded signals and thus improve the monitoring of the variable magnetic field. The possibility of varying the current passed through the winding of the electromagnet 20, in turn, makes it possible to vary the sensitivity of the device.

Figure 11:
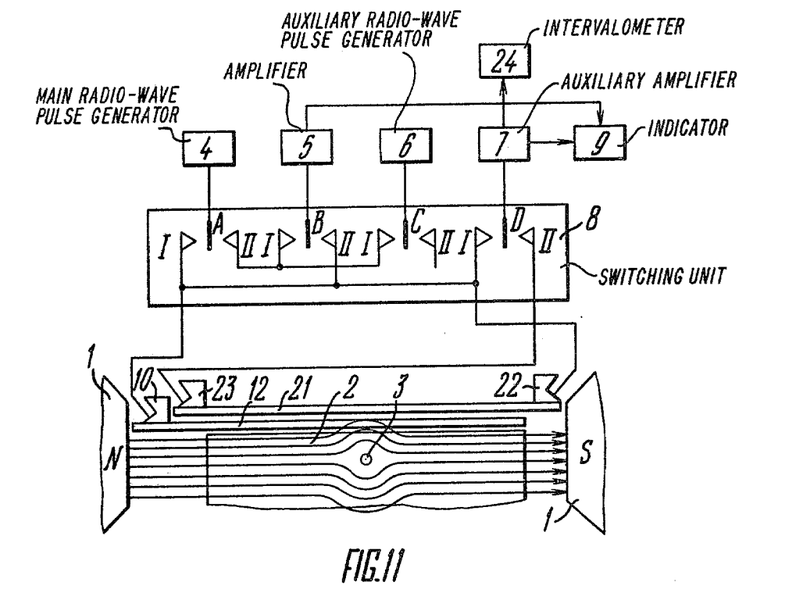
FIG. 11 is a schematic view of an alternative embodiment of the device according to the invention, which contains two coplanar strips.

FIG. 11 is a block diagram of a device in accordance with the invention, which is intended for the case when the magnetostrictive medium is acted upon by ultrasonic vibration. In this device, use is made of a second strip 21 which is identical to and coplanar with the strip 12 arranged in immediate proximity to the material 2 being tested. As in the embodiment of FIG. 6, the piezoelectric converter 10 is mounted on the strip 12; a second piezoelectric converter 22 is mounted on the second strip 21 on its side which is opposite to the converter 10. Another piezoelectric converter 23 is mounted on the strip 21 on that side thereof which is opposite to the converter 22. The converter 23 is connected via the switching unit 8 to the auxiliary amplifier 7. The functions of the piezoelectric converters 12, 21 and 23 can be performed by electromagnetic-acoustic converters. The device of FIG. 11 further contains an intervalometer 24 connected to the auxiliary amplifier 7.

Figure 12:
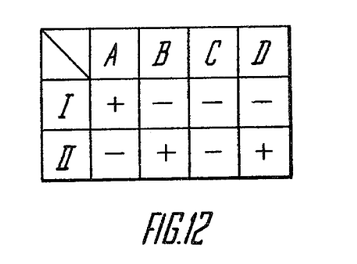
FIG. 12 shows the position of contacts of the switching unit to explain operation of the device according to FIG. 11.

The positions of the switches A, B, C and D of the switching unit 8 of the device of FIG. 11 are shown in FIG. 12. The converter 10 is connected to the main generator 4. The converter 22 is connected to the main amplifier 5. The converter 23 is connected to the auxiliary amplifier 7.

The main generator 4 and converter 10 produce ultrasonic vibrations in the strip 12, which modulate the static magnetic fields of the non-uniformities 3, extending throughout the strip 12. The ultrasonic modulation produces electromagnetic oscillations which, in turn, produce due to the magnetostriction, ultrasonic vibrations in the strip 21, which propagate in both directions from the non-uniformity 3 and are detected at the edges of the strip 21 by the converters 22 and 23.

The latter embodiment of the device is such that both the direct and reverse magnetostriction effects can be used to detect the non-uniformities 3. The direct magnetostriction effect is used to modulate the static magnetic fields. The reverse magnetostriction effect is used to have the electromagnetic oscillations to produce ultrasound in the strip 21.

Unlike all conventional testing methods, the method described above does not make it absolutely necessary to scan the material 2 being tested. For example, while testing articles of elongated shapes, such as rolled sheet articles, the sizes of the strips 12 and 21 may be selected to be greater than the width of the material 2 being tested. Thus the non-uniformities 3 are detected irrespective of their locations and the rate of inspection is significantly increased.

The arrangement of the converters 22 and 23 in the device of FIG. 11 is such that the distance covered by the ultrasonic wave from the converter 10 to the converter 22 is always constant (the wave travels across the strip 12 and then across the strip 21). As a result, the amplitude of the useful signal detected by the converter 22 is only dependent on the size of the non-uniformity 3. At the same time the distance covered by the signal before it reaches the converter 23 is determined by both the size and coordinates of the non-uniformity 3.

Thus the amplitude of the signal received by the converter 22 is indicative of the size of the non-uniformity, whereas the time it takes the signal to reach the converter 23, which is measured by the intervalometer 24, is indicative of the coordinates of the non-uniformity 3.

The methods and different versions of the device in accordance with the invention for detecting non-uniformities in magnetic materials make it possible to detect flaws in a wide range of materials, such as rolled metal, pipes, rods, wire, etc. The method and device of this invention are marked by a high accuracy and a high degree of noise immunity.

What is claimed is:

1. A method for detecting non-uniformities of magnetic materials, comprising the steps of placing a material to be tested in a magnetic field, acting on the surface of a magnetostrictive medium arranged in proximity to a non-uniformity zone of said material by ultrasonic vibration whereof the polarization vector contains a component normal to the surface of said material, and recording signals resulting from the electromagnetic-acoustic conversion in said magnetostrictive medium.

2. A method as claimed in claim 1, wherein said electromagnetic-acoustic conversion of said ultrasonic vibration of the prescribed polarization is effected in said magnetic field whereof the intensity corresponds to a maximum dynamic magnetostriction constant in said material being tested.

3. A method as claimed in claim 1, whereby the function of said magnetostrictive medium is performed by a first intermediate layer arranged in proximity to said material being tested, which first intermediate layer is acted upon by said ultrasonic vibration.

4. A method as claimed in claim 3, whereby the first intermediate layer is of a material whereof the dynamic magnetostriction constant is not lower than that of the permendur.

5. A method as claimed in claim 3, wherein the thickness of the first intermediate layer is selected at a preset frequency of said ultrasonic vibration with reference to dispersion curves of normal ultrasonic waves in said layer.

6. A method as claimed in claim 3, whereby the first intermediate layer is additionally magnetized at least in the recording zone, the lines of the additional magnetic field being perpendicular to the surface of said layer.

7. A method as claimed in claim 3, whereby a second intermediate layer similar to said first intermediate layer is arranged in proximity to said first intermediate layer, and ultrasonic vibration is detected in said second layer on the side opposite to the one on which said ultrasonic vibration acts on said first intermediate layer, the ultrasonic vibration in the second intermediate layer being caused by electromagnetic oscillation produced in said first intermediate layer opposite to said non-uniformity zone of said material being tested.

8. A method as claimed in claim 7, whereby the ultrasonic vibration in the second intermediate layer is also detected and recorded in the zone opposite to the zone where the first intermediate layer is acted upon.

9. A device for detecting non-uniformities of magnetic materials, comprising:
- a magnetostrictive medium arranged in proximity to said non-uniformity zone of said material being tested;
- a magnetizing system whereof the magnetic flux is passed through said magnetostrictive medium;
- a first converter mounted on the surface of said magnetostrictive medium and producing ultrasonic vibration to act upon said magnetostrictive medium;
- a second converter mounted on the surface of said magnetostrictive medium;
- a switching unit connected to said first and second converters;
- a radio-wave pulse generator connected via said switching unit to said first converter;
- an amplifier connected via said switching unit to said second converter;
- an indicator connected to said amplifier.

10. A device as claimed in claim 9, wherein said magnetostrictive medium is a first strip arranged in proximity to the surface of said material being tested.

11. A device as claimed in claim 10, wherein said material being tested has at least one bend and the surface of said first strip is congruent to that of said material being tested, while said second converter is constructed as at least one solenoid encompassing said first strip at the bend.

12. A device as claimed in clam 10, including a controlled electromagnet arranged in proximity to said second converter, the lines of its magnetic field being perpendicular to the surface of said first strip in the area where said second converter is located.

13. A device as claimed in claim 10, including a second strip identical to and coplanar with said first strip and carrying a second converter mounted on that side of said second strip which is opposite to said first converter mounted on said first strip.

14. A device as claimed in claim, 13, containing:
- an intervalometer connected to a second amplifier;
- a third converter mounted on said second strip on that side thereof which is opposite to said second converter, and connected via said switching unit to said second amplifier.

15. A method for detecting non-uniformities of magnetic materials, comprising the steps of placing a material to be tested in a magnetic field, acting on the surface of a magnetostrictive medium arranged in proximity to a non-uniformity zone of said material being tested by electromagnetic oscillation whereof the polarization vector is perpendicular to the vector of said magnetic field, and recording signals resulting from the electromagnetic-acoustic conversion in said magnetostrictive medium.

16. A method as claimed in claim 15, whereby said electromagnetic-acoustic conversion of said electromagnetic oscillation of the prescribed polarization is effected in said magnetic field whereof the intensity corresponds to a maximum dynamic magnetostriction constant of said material being tested.

17. A method as claimed in claim 15, whereby the function of said magnetostrictive medium is performed by an intermediate layer arranged in proximity to said material being tested, which intermediate layer is acted upon by said electromagnetic oscillation.

18. A method as claimed in claim 17, whereby said intermediate layer is of a material whereof the dynamic magnetostriction constant is not lower than that of the permendur.

19. A method as claimed in claim 17, whereby the thickness of said intermediate layer is selected at a predetermined frequency of said electromagnetic oscillation with reference to dispersion curves of normal ultrasonic waves in said layer.

20. A method as claimed in claim 17, whereby said intermediate layer is additionally magnetized at least in the recording zone, the lines of the additional magnetic field being perpendicular to the surface of said layer.

21. A device for detecting non-uniformities of magnetic materials, comprising:
- a magnetostrictive medium arranged in proximity to a non-uniformity zone of a material being tested;
- a magnetizing system whereof the magnetic flux is passed through said magnetostrictive medium;
- a first converter mounted on the surface of said magnetostrictive medium and generating electromagnetic oscillation to act upon said magnetostrictive medium;
- a second converter mounted on the surface of said magnetostrictive medium;
- a switching unit connected to said first and second converters;
- a radio-wave pulse generator connected via said switching unit to said first converter;
- an amplifier connected via said switching unit to said second converter;
- an indicator connected to said amplifier.

22. A device as claimed in claim 21, wherein said magnetostrictive medium is a strip arranged in proximity to said material being tested.

23. A device as claimed in claim 22, wherein said material being tested has at least one bend and the surface of said strip is congruent with that of said material being tested, said first converter being constructed as at least one solenoid encompassing said strip at the bend.

24. A device as claimed in claim 22, including a controlled electromagnet arranged in proximity to said first converter, its field lines being perpendicular to the surface of said strip in the area where said first converter is located.

25. A method for detecting non-uniformities of magnetic materials, comprising the steps of placing a material to be tested in a magnetic field, acting on the surface of a magnetostrictive medium arranged in proximity to a non-uniformity zone of said material by a combination of ultrasonic vibration whereof the polarization vector contains a component normal to the surface of said material being tested, and electromagnetic oscillation whereof the polarization vector is perpendicular to the vector of said magnetic field, and recording signals resulting from the electromagnetic-acoustic conversion in said magnetostrictive medium.

26. A method as claimed in claim 25, whereby said electromagnetic-acoustic conversion of said ultrasonic vibration and electromagnetic oscillation of the predetermined polarization is effected in said magnetic field whereof the intensity corresponds to a maximum dynamic magnetostriction constant in said material being tested.

27. A method as claimed in claim 25, whereby said magnetostrictive medium is an intermediate layer arranged in proximity to said material being tested and acted upon by said ultrasonic vibration and electromagnetic oscillation.

28. A method as claimed in claim 27, whereby said intermediate layer is of a material whereof the dynamic magnetostriction constant is not lower than that of the permendur.

29. A device as claimed in claim 27, whereby the thickness of said intermediate layer is selected at a predetermined frequency of said ultrasonic vibration and electromagnetic oscillation with reference to dispersion curves of normal ultrasonic waves in said layer.

30. A method as claimed in claim 27, whereby said intermediate layer is additionally magnetized in at least the recording zone, the lines of the additional magnetic field being perpendicular to the surface of said layer.

31. A device for detecting non-uniformities of magnetic materials, comprising:
   a magnetostrictive medium arranged in proximity to a non-uniformity zone of a material being tested;
   a magnetizing system whereof the magnetic flux is passed through said magnetostrictive medium;
   a first converter mounted on the surface of said magnetostrictive medium and generating ultrasonic vibration to act upon said magnetostrictive medium;
   a second converter mounted on the surface of said magnetostrictive medium and generating electromagnetic oscillation to act upon said magnetostrictive medium;
   a switching unit connected to said first and second converters;
   a first radio-wave pulse generator connected via said switching unit to said first converter;
   a second radio-wave pulse generator connected via said switching unit to said second converter;
   a first amplifier connected via said switching unit to said second converter;
   a second amplifier connected via said switching unit to said first converter;
   an indicator connected in parallel with said first and second amplifiers.

32. A device as claimed in claim 31, wherein said magnetostrictive medium is a strip arranged in proximity to the surface of said material being tested.

33. A device as claimed in claim 32, wherein said strip is shaped as a disc and said second converter is placed in the center of said disc.

34. A device as claimed in claim 33, including:
   a pulse counter connected to said first amplifier;
   a comparator connected to said first amplifier.

35. A device as claimed in claim 32, wherein said material being tested has at least one bend and the surface of said strip is congruent with that of said material being tested, while said second converter is constructed as at least one solenoid encompassing said strip at the bend.

36. A device as claimed in claim 32, including a controlled electromagnet arranged in proximity to said second converter, its field lines being perpendicular to the surface of said strip in the area where said second converter is located.

* * * * *